United States Patent [19]

Brown

[11] Patent Number: 4,608,380

[45] Date of Patent: Aug. 26, 1986

[54] SUBSTITUTED AMINOPYRIDONES HAVING HISTAMINE H$_2$-RECEPTOR BLOCKING ACTIVITY

[75] Inventor: Thomas H. Brown, Tewin, England

[73] Assignee: Smith Kline & French Laboratories Limited, Welwyn Garden City, England

[21] Appl. No.: 675,661

[22] Filed: Nov. 28, 1984

[30] Foreign Application Priority Data

Dec. 1, 1983 [GB] United Kingdom ............... 8332091

[51] Int. Cl.$^4$ .................. C07D 211/86; A61K 31/44; A61K 31/445

[52] U.S. Cl. .................................. 514/318; 514/332; 514/333; 514/340; 514/153; 514/165; 546/194; 546/256; 546/275; 546/281

[58] Field of Search ............. 546/194, 275, 256, 281; 514/318, 332, 333, 340, 343

[56] References Cited

U.S. PATENT DOCUMENTS

| | | | |
|---|---|---|---|
| 3,932,644 | 1/1976 | Durant et al. | 514/341 |
| 4,309,433 | 1/1982 | Hirai et al. | 514/343 |
| 4,385,058 | 5/1983 | Cooper et al. | 514/272 |
| 4,439,437 | 3/1984 | Jones et al. | 514/342 |
| 4,496,567 | 1/1985 | Brown et al. | 514/272 |

OTHER PUBLICATIONS

Derwent Abstract, 44455 D/25 (EP 30,092).

Primary Examiner—Alan L. Rotman
Attorney, Agent, or Firm—Joan S. Keps; Stuart R. Suter; Alan D. Lourie

[57] ABSTRACT

This invention relates to 2-substituted aminopyridone compounds which have histamine H$_2$-antagonist activity.

21 Claims, No Drawings

SUBSTITUTED AMINOPYRIDONES HAVING HISTAMINE $H_2$-RECEPTOR BLOCKING ACTIVITY

This invention relates to pyridone derivatives, and in particular to such derivatives comprising a Mannich group. This invention further relates to pharmaceutical compositions containing these compounds and to methods of blocking histamine $H_2$-receptors by administering these compounds.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427 (1966) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

Accordingly the present invention provides compounds of the formula (I):

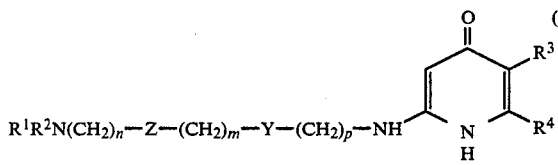

and a pharmaceutically acceptable salt thereof, wherein
$R^1$ and $R^2$ are independently hydrogen, $C_{1-6}$alkyl, aryl($C_{1-6}$)alkyl, heteroaryl($C_{1-6}$)alkyl, $C_{3-10}$cycloalkyl, hydroxy($C_{2-6}$)alkyl or halo($C_{2-6}$)alkyl, (wherein said hydroxy and halo groups are not substituted on the carbon atom adjacent to the nitrogen atom); or
$R^1$ and $R^2$ together represent $-(CH_2)_q-$ wherein q is 4 to 7, to form together with the nitrogen atom to which they are attached a 5-8 membered saturated ring, optionally substituted by $C_{1-6}$alkyl;
n is an integer from 1 to 6;
Z is 1,3-phenylene, 1,4-phenylene, 2,4-pyridyl (wherein the $R^1R^2N(CH_2)_n$ group is in the 4-position);
m is zero or one;
Y is oxygen, sulphur or methylene;
p is two, three or four; and
$R^3$ is hydrogen, $C_{1-6}$alkyl or aryl($C_{1-6}$)alkyl and $R^4$ is hydrogen or $C_{1-6}$alkyl; or $R^3$ and $R^4$ together with the carbon atoms to which they are attached form a benzene ring optionally substituted by $C_{1-6}$alkyl.

When used herein alkyl means groups that are either straight-chained or branched. In general preferred alkyl groups are methyl and ethyl.

Suitably in the definitions of $R^1-R^3$, aryl($C_{1-6}$)alkyl is phenyl($C_{1-6}$)alkyl and heteroaryl($C_{1-6}$)alkyl is furanyl($C_{1-6}$)alkyl or thienyl($C_{1-6}$)alkyl.

Suitably $R^1$ is aryl($C_{1-6}$)alkyl for example benzyl or phenethyl, heteroaryl($C_{1-6}$)alkyl for example furanylmethyl or thienylmethyl, halo($C_{2-6}$)alkyl for example 2,2,2-trifluoroethyl, or $C_{3-10}$cycloalkyl for example cyclohexyl. More suitably $R^1$ is $C_{1-6}$alkyl, for example methyl, ethyl or propyl.

Suitably $R^2$ is hydrogen or $C_{1-6}$alkyl, for example methyl, ethyl or propyl.

Suitably $R^1$ and $R^2$ have the same value, for example they both are methyl or they are both ethyl. In another suitable aspect $R^1$ and $R^2$ together with the nitrogen atom to which they are attached form a pyrrolidino, piperidino or hexahydroazepino ring. In a preferred aspect $R^1R^2N-$ represents a piperidino ring.

Preferably n is one.

Suitably Z is 1,3-phenylene or 2,4-pyridyl. Favourably when Z is 1,3-phenylene, m is zero and preferably Y is oxygen. Favourably when Z is 2,4-pyridyl m is one and preferably Y is sulphur. In an alternative favourable aspect when Z is 2,4-pyridyl, m is zero and preferably Y is oxygen.

Suitably m and p when added together equals three, that is suitably p is two when m is one, and suitably p is three when m is zero.

Examples of favoured groups $R^1R^2N(CH_2)_n-Z-(CH_2)_m-Y-(CH_2)_p$ include:
4-dimethylaminomethylpyrid-2-ylmethylthioethyl,
4-piperidinomethylpyrid-2-ylmethylthioethyl,
4-dimethylaminomethylpyrid-2-yloxypropyl,
4-piperidinomethylpyrid-2-yloxypropyl,
3-dimethylaminomethylphenoxypropyl,
3-piperidinomethylphenoxypropyl,
3-dimethylaminomethylphenylmethylthioethyl or
3-piperidinomethylphenylmethylthioethyl.

Suitably $R^3$ is hydrogen, $C_{1-6}$alkyl for example methyl, ethyl, propyl or butyl, or aryl($C_{1-6}$)alkyl for example benzyl or phenethyl.

Suitably $R^4$ is hydrogen.

In a preferred aspect $R^3$ and $R^4$ are both hydrogen.

In an alternative preferred aspect $R^3$ and $R^4$ together with the carbon atoms to which they are attached form a benzene ring.

The compounds of the formula (I) are depicted in the 4(H) tautomeric form, and exist in equilibrium with other tautomeric forms, for example:

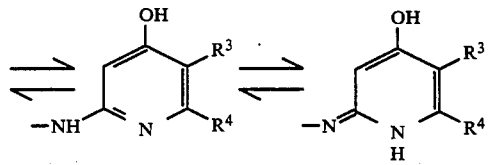

The present invention covers all isomeric and tautomeric forms of the compounds of the formula (I).

Specific preferred compounds of this invention include:

2-[3-[3-(piperidinomethyl)phenoxy]propylamino]pyrid-4-one,
2-[3-[3-(pyrrolidinomethyl)phenoxy]propylamino]pyrid-4-one,
2-[3-[3-(hexahydroazepinomethyl)phenoxy]-propylamino]pyrid-4-one,
2-[3-[3-(piperidinomethyl)phenoxy]propylamino]-4-quinolone, and
2-[3-[4-(piperidinomethyl)pyrid-2-yloxy]propylamino]-pyrid-4-one,
and pharmaceutically acceptable salts thereof.

The activity of the compounds of the formula (I) as histamine H₂-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine H₁-receptors.

The histamine H₂-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

The measurement of inhibition of histamine-stimulated secretion of gastric acid from the lumen-perfused stomachs of rats anaesthetised with urethane, and the measurement of inhibition of histamine-induced tachycardia in the isolated guinea pig right atrium, are detailed in U.S. Pat. No. 4,385,058.

To illustrate the level of activity of the compounds of the invention we have determined that where tested the products of the Examples have ED₅₀ values in the lumen-perfused rat test of less than one micromol kg$^{-1}$ i.v. and pA₂ values in the guinea pig atrium test of more than six. The compound of Example 1 is over 100 times more active in these tests than 2-[2-(5-methylimidazol-4-ylmethylthio)ethylamino]pyrid-4-one, that is Example 16 of U.S. Pat. No. 3,932,644. Furthermore the compound of Example 1 shows a longer duration of activity than cimetidine after intravenous administration in the Heidenhain pouch dog when dose levels had been adjusted to produce similar peak responses.

In order to use the compounds of the formula (I) or pharmaceutically acceptable salts thereof for medical purposes, they are normally formulated in accordance with standard pharmaceutical practice as pharmaceutical compositions.

The invention further provides pharmaceutical compositions comprising a compound of the formula (I) or a pharmaceutically acceptable salt thereof together with a pharmaceutically acceptable carrier.

The compounds of the formula (I) and pharmaceutically acceptable salts thereof may be administered orally, parenterally, cutaneously or rectally.

The compounds of the formula (I) and pharmaceutically acceptable salts thereof which are active when given orally can be formulated as syrups, tablets, capsules and lozenges. A syrup formulation will generally consist of a suspension or solution of the compound or salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or pharmaceutically acceptable salt thereof in a sterile aqueous carrier or parenterally acceptable oil.

Typical compositions for administration to the skin include lotions and creams in which the compound of the formula (I) or pharmaceutically acceptable salt thereof is contained in a liquid vehicle.

A typical suppository formulation comprises a compound of the formula (I) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably 0.5 to 25 mg) of a compound of the formula (I) or a pharmaceutically acceptable salt thereof calculated as the free base.

The invention also provides a method of blocking histamine H₂-receptors which comprises administering to an animal an effective amount to block and receptors of a compound of the formula (I) or pharmaceutically acceptable salt thereof.

The pharmaceutical compositions of this invention will normally be administered to a subject for the treatment of peptic ulcers and other conditions caused or exacerbated by gastric acidity in the same general manner as that employed for known histamine H₂-antagonists, due allowance being made in terms of dose levels for the potency of the compound of the present invention relative to known histamine H₂-antagonists. The daily dosage regimen for an adult patient is an oral dose of between 15 mg and 1500 mg, preferably between 15 mg and 250 mg, or an intravenous, subcutaneous, or intramuscular dose of between 0.5 mg and 150 mg, preferably between 1.0 mg and 20 mg, of a compound of the formula (I) or pharmaceutically acceptable salt thereof calculated as the free base, the composition being administered 1 to 6 times per day, suitably 1 to 4 times a day.

The compounds of the formula (I) and pharmaceutically acceptable salts thereof may be prepared by a process which comprises:

(a) reacting a compound of the formula (II) with a compound of the formula (III):

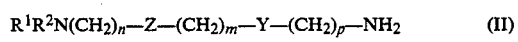

$$R^1R^2N(CH_2)_n-Z-(CH_2)_m-Y-(CH_2)_p-NH_2 \quad (II)$$

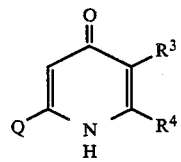

(III)

wherein R¹, R², R³, R⁴, Z, m, n and p are as hereinbefore defined, and Q is a group displaceable by amine; or (b) reducing a compound of the formula (IV) or (V):

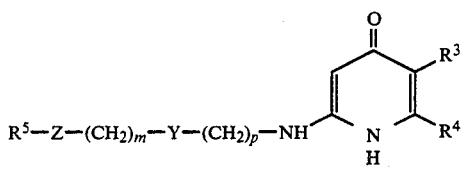 (IV)

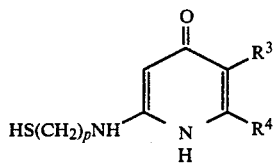 (XI)

wherein $R^1$, $R^2$, $R^3$, $R^4$, n, Z and p are as hereinbefore defined, and $Q^3$ is a group displaceable by thiol or chemical equivalent thereof; or (f) deprotecting a compound of the formula (XII):

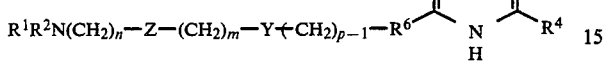 (V)

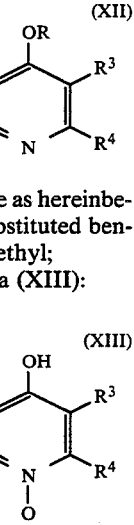 (XII)

wherein $R^1$, $R^2$, $R^3$, $R^4$, Z, Y, n, m and p are as hereinbefore defined, $R^5$ is a group reducible to a group $R^1R^2N(CH_2)_n$— and $R^6$ is a group —CONH— or —C=NH—; or (c) for preparing compounds wherein Z is phenylene, m is zero and Y is oxygen, reacting a compound of the formula (VI) or chemical equivalent thereof with a compound of the formula (VII):

wherein $R^1$, $R^2$, $R^3$, $R^4$, n, Z, m, Y and p are as hereinbefore defined and R is $C_{1-6}$alkyl, benzyl, substituted benzyl, allyl, 2,2,2-trichloroethyl or methoxyethyl;

(g) reducing a compound of the formula (XIII):

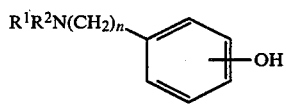 (VI)

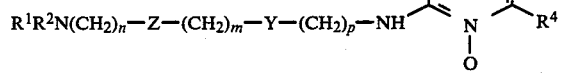 (XIII)

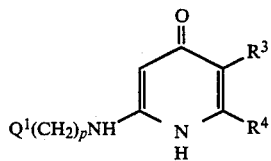 (VII)

wherein $R^1$, $R^2$, $R^3$, $R^4$, n, Z, m, Y and p are as hereinbefore defined;

and optionally thereafter forming a pharmaceutically acceptable salt.

wherein $R^1$, $R^2$, $R^3$, $R^4$, n and p are as hereinbefore defined, and $Q^1$ is a group displaceable by phenol or chemical equivalent thereof; or (d) for preparing compounds wherein m is one and Y is sulphur, reacting a compound of the formula (VIII) or chemical equivalent thereof with a compound of the formula (IX):

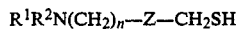 (VIII)

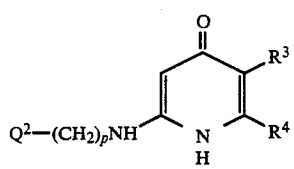 (IX)

wherein $R^1$, $R^2$, $R^3$, $R^4$, Z, n and p are as hereinbefore defined, and $Q^2$ is a group displaceable by thiol or chemical equivalent thereof; or (e) for preparing compounds wherein m is one and Y is sulphur, reacting a compound of the formula (X) with a compound of the formula (XI) or chemical equivalent thereof:

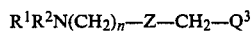 (X)

Suitably Q is chloro or bromo. Favourably Q is bromo.

The reaction between a compound of the formula (II) and a compound of the formula (III) can be performed in the absence of solvent at an elevated temperature, or in the presence of a substantially inert solvent such as a polar solvent, for example a pyridine or anisole, or dimethylformamide at for example a temperature between ambient and reflux, preferably reflux. When Q is bromo the reaction for example may be performed at 140°-180° C. in the absence of solvent.

In the compounds of the formula (IV) in one suitable aspect $R^5$ is a group $R^1R^2N$—$(CH_2)_x$—CO—$(CH_2)_y$— wherein $x+y=n-1$. Favourably x and y are both zero so that the group $R^1R^2NCO$— is a precursor to the group $R^1R^2NCH_2$—. The reduction of such a group $R^1R^2N$—$(CH_2)_x$—CO—$(CH_2)_y$— may be performed with a hydride for example lithium aluminum hydride.

In an alternative process $R^5$ is a group CHO—$(CH_2)_{n-1}$—, which may be converted to a group $R^1R^2N(CH_2)_n$— on reaction with an amine $R^1R^2NH$ under conditions of reductive amination. Furthermore in another suitable aspect $R^5$ may be a group $HO(CH_2)_n$— which may be converted directly to $R^1R^2N(CH_2)_n$—, or indirectly thereto for example via a moiety such as $Br(CH_2)_n$— and thence to $R^1R^2N(CH_2)_n$—. Such transformations may be carried out in conventional manner.

The compounds of the formula (V) may be reduced to form compounds of the formula (I), for example using lithium aluminium hydride in an ether solvent when $R^6$ is —CONH—; and for example using a borohydride in an alkanol, lithium aluminium hydride in an ether solvent, or catalytically hydrogenating when $R^6$ is —CH=N—.

In the reaction between the compounds of the formulae (VI) and (VII) suitably $Q^1$ is chloro or bromo. Suitably the reaction is performed under basic conditions, for example the anion of the compound of the formula (VI) may be generated, for example using sodium hydride. The reaction is performed in a suitable aprotic solvent for example dimethylformamide at a non-extreme temperature for example between 0° C. and 100° C., suitably between ambient and 70° C.

Suitably in the reaction between the compounds of the formulae (VIII) and (IX) $Q^2$ is chloro, bromo, arylsulphonyloxy for example 4-methylbenzenesulphonyloxy or $C_{1-6}$alkylsulphonyloxy for example methanesulphonyloxy. Such reactions are generally performed in the presence of a base for example triethylamine, an alkoxide or a hydroxide.

Suitably in the reaction between the compounds of the formula (X) and (XI) $Q^3$ is chloro, bromo, hydroxy, $C_{1-6}$alkoxy for example methoxy, $C_{1-6}$alkanoyloxy for example acetoxy, arylsulphonyloxy for example 4-methylbenzenesulphonyloxy, or $C_{1-6}$alkylsulphonyloxy for example methanesulphonyloxy.

Preferably $Q^3$ is hydroxy in which case the reaction between the compounds of the formulae (X) and (XI) is performed under acidic conditions. When $Q^3$ is chloro or bromo it is preferable to perform the reaction in the presence of a strong base for example sodium ethoxide in ethanol. When $Q^3$ is an arylsulphonyloxy or alkylsulphonyloxy group the reaction is preferably performed under mildly basic conditions for example in pyridine solution.

The deprotection of a compound of the formula (XII) is performed by conventional methods, for example by chemical or enzymic hydrolysis or by hydrogenolysis, see McOmie "Protecting Groups in Organic Synthesis", for example compounds of the formula (XII) wherein R is allyl, benzyl or substituted benzyl such as nitrobenzyl or alkylbenzyl can be converted to compounds of the formula (I) via catalytic hydrogenation preferably using hydrogen gas. Suitable catalysts include conventional transition metal catalysts for example palladium on a carrier suitably about 10% palladium on charcoal, or Raney nickel. The hydrogenation can be performed at non-extreme pressure, for example at atmospheric pressure or at pressures up to 10 atmospheres ($10.13 \times 10^5$ Pa). In an alternative particular aspect where R is benzyl, methoxyethyl, 2,2,2-trichloroethyl or $C_{1-6}$alkyl in the compounds of the formula (XII) hydrolysis to compounds of the formula (I) can be achieved by acidic hydrolysis at an elevated temperature, for example mineral acid such as concentrated hydrochloric acid at elevated temperature for example under reflux conditions.

The N-oxides of the formula (XIII) can be reduced to the compounds of the formula (I) in conventional manner. For example using a phosphorus reagent such as phosphorus tribromide or phosphorus trichloride, or a sulphur reagent such as $S_8$, $SO_2$, a dialkylsulphide, sodium sulphite or sodium hydrosulphite. In alternative aspects the reduction can be conventionally performed using iron in acetic acid, zinc in dilute acid, catalytic hydrogenation for example using palladium on carbon, or Raney nickel. In a preferred aspect the reduction is performed using phosphorus tribromide.

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Suitable pharmaceutically acceptable acid addition salts of the compounds of the formula (I) include those formed with hydrochloride, hydrobromic, sulphuric, phosphoric, acetic, citric, maleic, lactic, ascorbic, fumaric, oxalic, methanesulphonic and ethanesulphonic acids.

The compounds of the formulas (II), (III), (VIII) and (X) are known to the art or are prepared by known methods such as by the methods of U.S. Pat. Nos. 3,932,644 and 4,385,058 and European Patent Application Publication Nos. 13071 and 89153.

The compounds of the formula (IV) may be prepared in a manner analogous to that described for the preparation of compounds of the formula (I), for example reacting a compound of the formula (III) with an analogue of a compound of the formula (II) wherein $R^1R^2N(CH_2)_n$— is replaced by $R^5$; provided that $R^5$ is suitably protected as necessary.

The compounds of the formula (V) wherein $R^6$ is CH=N may be prepared by the reaction of a compound of the formula (XIV) with a compound of the formula (XV):

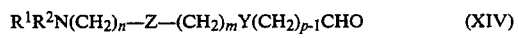

$$R^1R^2N(CH_2)_n-Z-(CH_2)_mY(CH_2)_{p-1}CHO \qquad (XIV)$$

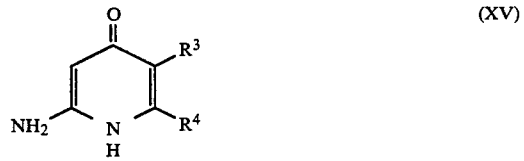

(XV)

wherein $R^1$, $R^2$, $R^3$, $R^4$, n, m, Z, Y and p are as hereinbefore defined, optionally in the presence of an acid catalyst. The compounds of the formula (V) wherein $R^6$ is —CONH— may be prepared by the reaction of a compound of the formula (XV) with an activated derivative of a compound of the formula (XVI):

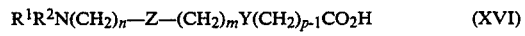

$$R^1R^2N(CH_2)_n-Z-(CH_2)_mY(CH_2)_{p-1}CO_2H \qquad (XVI)$$

wherein $R^1$, $R^2$, $R^3$, $R^4$, n, m, Z, Y and p are as hereinbefore defined. Suitable active derivatives are acyl halides, anhydrides and activated esters. The aldehydes of the formula (XIV) and the acids of the formula (XVI) and derivatives thereof may be prepared in a manner similar to that of GB 2030979A.

The compounds of the formula (VI) are preparable for example by the methods of Turner et al J. Org. Chem. 24 p 1952 (1959).

The compounds of the formulae (VII), (IX) and (XI) can be prepared for example by methods analogous to that described for the reaction of compounds of the formulae (II) and (III). For example compounds of the formula (III) can be reacted with hydroxyalkylamine optionally protected on the hydroxy function; the hydroxy function can be deprotected if required, and subsequently the compound is converted to a compound of the formula (VII) or (IX) using conventional methods. For example to make compounds of the formula (XI) wherein p is 2 the compounds of the formula (III) are reacted with cysteamine optionally protected on the thiol function.

The compounds of the formula (XII) can be prepared by the methods analogous to those described for preparing compounds of the formula (I). Suitably R is benzyl or $C_{1-6}$alkyl for example methyl or ethyl. For example a compound of the formula (II) can be reacted with 2-chloro-4-ethoxyquinolone to form a compound of the formula (XII) wherein R is ethyl and $R^3$ and $R^4$ are joined. In an alternative the compounds of the formula (XII) may be prepared by reducing a compound of the formula (XVII):

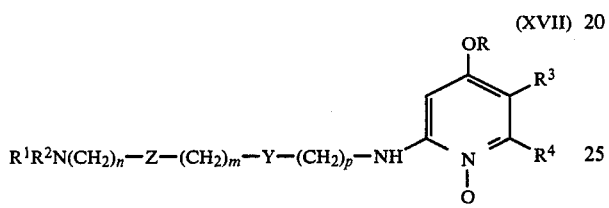

wherein $R^1$, $R^2$, $R^4$, Z, Y, m, n, p and R are as hereinbefore defined, in an appropriate manner similar to those described for converting a compound of the formula (XIII) to a compound of the formula (I). Dependent on the nature of the reagent and the nature of R, it is possible that a compound of the formula (XVII) will form either a compound of the formula (XII) or a compound of the formula (XIII) either of which may react further in situ to provide a compound of the formula (I). The compounds of the formula (XVII) can be prepared for example by reacting a compound of the formula (II) with a compound of the formula (XVIII):

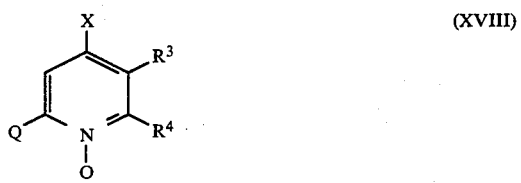

wherein Q, $R^3$ and $R^4$ are as hereinbefore defined and X is a group convertible to RO—, for example nitro; and thereafter converting the group X to a group RO— as hereinbefore defined, for example using sodium benzylate in dimethylformamide.

The compounds of the formula (XIII) can be prepared from a compound of the formula (XVII) in a manner analogous to that described above for converting compounds of the formula (XII) to compounds of the formula (I).

The following Examples serve to illustrate this invention.

EXAMPLE 1

2-[3-[3-(Piperidinomethyl)phenoxy]propylamino]-pyrid-4-one

3-[3-(Piperidinomethyl)phenoxy]propylamine (14.84 g) and 2-bromopyrid-4-one (5.20 g) were stirred together at 165°–170° C. for 4 hours. The reaction mixture was cooled to give a dark orange glassy solid which was dissolved in 2N hydrochloric acid to give a solution having a pH of 4.5. This solution was washed thoroughly with diethyl ether (8×) and chloroform (4×) to remove residual 2-bromopyrid-4-one and some by-product. The aqueous phase was taken to pH 9–10 with 2N sodium hydroxide and extracted into chloroform (9×). The chloroform extracts were combined, dried and evaporated under reduced pressure to afford a dark orange oil. This oil was subjected to medium pressure column chromatography on silica gel using gradient elution; ethyl acetate→10% methanol:90% ethyl acetate. The desired fractions were collected, combined and evaporated under reduced pressure to give the title compound (6.0 g) as a yellow-orange oil which was washed with diethyl ether.

This oil was dissolved in a minimum quantity of hot ethanol, treated with a solution of maleic acid (4.15 g) in hot ethanol, cooled and the resultant crystals collected by filtration. Recrystallisation from ethanol afforded 2-[3-[3-(piperidinomethyl)phenoxy]propylamino]-pyrid-4-one dimaleate (3.2 g), m.p. 146°–146.5° C.

EXAMPLE 2

2-[3-[3-(Pyrrolidinomethyl)phenoxy]propylamino]pyrid-4-one

In a manner similar to that of Example 1, 3-[3-(pyrrolidinomethyl)phenoxy]propylamine (4.69 g) and 2-bromopyrid-4-one (1.74 g) gave the title compound as an oil (1.54 g), after medium pressure column chromatography using chloroform-methanol gradient elution. This oil was dissolved in ethanol, treated with maleic acid (1.10 g) in ethanol and crystallised from isoprpanol to afford 2-[3-[3-(pyrrolidinomethyl)phenoxy]-propylamino]pyrid-4-one dimaleate (0.67 g), m.p. 115°–8° C.

EXAMPLE 3

2-[3-[3-(Hexahydroazepinomethyl)phenoxy]-propylamino]pyrid-4-one

3-[3-(Hexahydroazepinomethyl)phenoxy]propylamine (6.32 g) and 2-bromopyrid-4-one (1.4 g) were stirred together at 165°–170° C. for four hours. The reaction mixture was cooled, dissolved in dilute HCl and washed with ethyl acetate. The aqueous layer was taken to pH 13–14 with sodium hydroxide, washed with ethyl acetate, adjusted to pH 8–9 with dilute HCl and extracted into ethyl acetate. This latter ethyl acetate extracts was dried (MgSO4) and evaporated under reduced pressure to give the title compound as an oil (0.36 g). This was dissolved in hot ethanol, treated with maleic acid in ethanol and crystallised from ethanol to give 2-[3-[3-(hexahydroazepinomethyl)phenoxy]-propylamino]pyrid-4-one dimaleate (0.135 g), m.p. 141°–3° C. (recrystallised from isopropanol).

EXAMPLE 4

2-[3-[3-(Piperidinomethyl)phenoxy]propylamino]-4-quinolone (i) 3-[3-(Piperidinomethyl)phenoxy]propylamine (9.93 g) and 2-chloro-4-ethoxyquinoline (4.15 g) were heated, with stirring, at 160° C. for 4¼ hours. The reaction mixture was cooled to give a glass which was dissolved in dilute HCl to give a solution having a pH of 6. This solution was washed with diethyl ether (2×), taken to pH 5 and extracted continuously into chloroform. The chloroform extract was evaporated under reduced pressure to give a residue which was dissolved in water, taken to pH 9 with aqueous NaHCO$_3$, and extracted into diethylether (7×) and chloroform (2×). These extracts were dried (MgSO$_4$) and evaporated to give 2-[3-[3-(piperidinomethyl)phenoxy]propylamino]-4-ethoxyquinoline as an oil (7.92 g). This was dissolved in hot ethanol and treated with maleic acid in ethanol to give the dimaleate salt (7.53 g), m.p. 145.5°–147.5° C. (recrystallised from ethanol).

(ii) 2-[3-[3-(Piperidinomethyl)phenoxy]propylamino]-4-ethoxyquinoline (liberated from the dimaleate (3.0 g)) was stirred under reflux in concentrated hydrochloric acid (30 ml) for 4½ hours. The reaction mixture was cooled, reduced in volume by evaporation under reduced pressure, taken to pH 9 (aqueous NaHCO$_3$), washed with ether, and extracted into chloroform (3×). The chloroform extracts were combined, dried (MgSO$_4$), evaporated under reduced pressure and the resultant white oil was treated with hot ethylacetate to give the title compound (0.89 g), m.p. 171°–171.5° C. (recrystallised from methanol).

EXAMPLE 5

2-[3-[4-(Piperidinomethyl)pyrid-2-yloxy]propylamino]-pyrid-4-one (i) 3-[3-(Piperidinomethyl)pyrid-2-yloxy]propylamine (37.4 g), 2-chloro-4-nitropyridine-N-oxide (20.0 g) and triethylamine (42 ml) were stirred under reflux in ethanol for 3 hours. The reaction mixture was partially cooled, methanol (50 ml) added and on further cooling crystals formed, were collected and dried. These were dissolved in dilute HCl, washed with ether (9×), taken to pH 9 (aqueous NaHCO$_3$ and extracted into chloroform (3×). The chloroform extracts were dried (MgSO$_4$) and evaporated under reduced pressure to give a solid. Under methanol this formed crystals of 2-[3-[4-(piperidinomethyl)pyrid-2-yloxy]propylamino]-4-nitropyridine-N-oxide (12.98 g), m.p. 115°–6° C.

(ii) Benzyl alcohol (3.21 ml; 0.031 mol) was added dropwise to a stirred suspension of sodium hydride dispersion in oil (50%; 1.49 g; 0.031 mol) in dimethylformamide (100 ml) under nitrogen. The mixture was stirred for 50 minutes at room temperature and part of the product of (i) above (6.00 g) in dimethylformamide (150 ml) was added. The resultant mixture was stirred and heated at 80° C. for 4 hours, further benzyl alcohol (5 ml) and sodium hydride (0.18 g) added, heated at 80° C. for a further 3 hours, and heated at 90° C. for a further hour. The reaction mixture was cooled and poured on to ice to give an aqueous solution (1 L). This was extracted with ethyl acetate (3×), the combined organic extracts were washed with water and extracted with 2N HCl (3×). The combined acid extracts were washed with ethyl acetate, basified to pH 9–10 with 50% NaOH, and re-extracted into ethyl acetate (3×). The combined latter ethyl acetate extracts were combined and dried to give yellow crystals which were recrystallised to give 2-[3-[4-(piperidinomethyl)pyrid-2-yloxy]propylamino]-4-benzyloxypyridine-N-oxide (2.02 g), m.p. 148.5° C. (recrystallised from acetone or ethyl acetate).

(iii) To part of the product from (ii) above (1.10 g) in ethanol (100 ml) was added Raney nickel suspended in ethanol. This mixture was subjected to hydrogenation for 4½ hours (initial hydrogen pressure (358 kPa (52 p.s.i.)). The mixture was filtered, evaporated under reduced pressure and the residue triturated under diethyl ether to give 2-[3-[4-(piperidinomethyl)pyrid-2-yloxy]propylamino]pyrid-4-one (0.5 g), m.p. 127°–8° C. (recrystallised from ethyl acetate).

EXAMPLE 6

2-[3-[3-(Piperidinomethyl)phenoxy]propylamino]pyrid-4-one (i) 3-[3-(Piperidinomethyl)phenoxy]propylamine (6.21 g), 2-chloro-4-nitropyridine-N-oxide (4.36 g) and triethylamine (6.32 g) were stirred, in ethanol (30 ml), under reflux for 3½ hours. The reaction mixture was cooled gradually to 0° C. to yield 2-[3-[3-(piperidinomethyl)phenoxy]propylamino]-4-nitropyridine-N-oxide (4.23 g), m.p. 90°–90.5° C.

In an alternative method the 0.8 hydrobromide/0.2 hydrochloride salt of the above N-oxide may be prepared as below.

3-[3-(Piperidinomethyl)phenoxy]propylamine (16.67 g, 0.047 mol), 2-bromo-4-nitropyridine-N-oxide (9.91 g, 0.0453 mol) and triethylamine (14 ml, 0.10 mol) were stirred under reflux in ethanol (90 ml) for 6 hours. Ethanol was removed under reduced pressure to give an oil which was dissolved in 2N-hydrochloric acid to give a solution of pH 3 (adjustment with 2N-sodium hydroxide solution necessary). The solution was exhaustively extracted with chloroform, and the combined, dried chloroform layers were concentrated under reduced pressure to an oily solid, which was left under a small amount of methanol overnight. Resultant yellow crystals (11.7 g, 56%) were filtered and washed with cold methanol to give 2-[3-[3-(piperidinomethyl)phenoxy]-propylamino]-4-nitropyridine-N-oxide 0.8 hydrobromide-0.2 hydrochloride, m.p. 197°–8° C. (recrystallised from ethanol).

(ii) Benzylalcohol (0.99 g, 0.95 ml, 0.0092 mol) was added dropwise to a suspension of sodium hydride (0.37 g, 0.0076 mol) (50% dispersion in oil) in dimethylformamide (20 ml) at room temperature under nitrogen. The mixture was stirred at room temperature for 30 minutes then 2-[3-[3-(piperidinomethyl)phenoxy]propylamino-4-nitropyridine-N-oxide (as 0.8 hydrobromide-0.2 hydrochloride salt) (1.4 g, 0.003 mol) suspended in dimethylformamide (30 ml) was added. To the dark blue mixture (containing anion) was therefore added more benzyl alcohol (5 ml, excess) and the mixture heated to 80° C. for 2 hours. After this time reaction was still incomplete, but was completed 5 minutes after addition of sodium hydride (0.37 g., 0.0076 mol).

The brown solution was poured into water (250 ml), extracted with ethyl acetate (3×50 ml) and the combined extracts were washed with a little water and extracted into 2N-hydrochloric acid (3×35 ml). The acid extracts were washed with ethyl acetate (50 ml) and adjusted to pH 10 with 50% sodium hydroxide solution then re-extracted into ethyl acetate (3×25 ml). The combined organic extracts were washed with brine, dried and concentrated under reduced presssure to give, as a brown gum-like solid, 2-[3-[3-(piperidinomethyl)phenoxy]propylamino]-4-benzyloxypyridine-N-oxide, (1.1 g). Recrystallisation from dichloromethane/40°–60° C. petroleum ether gave 2-[3-[3-(piperidinomethyl)phenoxy]propylamino-4-benzyloxypyridine-N-oxide.

In a similar manner the 4-nitropyridine-N-oxide free base (1.55 g) was converted to the 4-benzyloxypyridine-4-oxide (1.1 g), m.p. 143°–145.5° C. (recrystallised from dichloromethane/40°–60° C. petroleum ether).

(iii) Part of the product from (ii) above (1.10 g) in ethanol (100 ml) was subjected to hydrogenation at 344 kPa (50 p.s.i.) in the presence of Raney nickel (approx. 0.1 g). After 5 hours the reaction mixture was filtered and washed with ethanol. The filtrate was evaporated under reduced pressure to give 2-[3-[3-(piperidinomethyl)phenoxy]propylamio-4-benzyloxypyridine (1.07 g) as an oil. This was dissolved in ether and treated with maleic acid in ethanol to give the dimaleate salt (1.08 g), m.p. 145.5°–147.5° C. (recrystallised from ethanol).

(iv) Part of the dimaleate product from (iii) above (0.1 g) was stirred under reflux for 30 minutes in concentrated hydrochloric acid (3 ml), and kept overnight at 0° C. Maleic acid was filtered off and the filtrate evaporated to give, as an oil, 2-[3-[3-(piperidinomethyl)phenoxy]propylamino]pyrid-4-one (identical by chromatography with the product of Example 1).

EXAMPLE 7

2-[3-[3-(Piperidinomethyl)phenoxy]propylamino]pyrid-4-one

2-[3-[3-(Piperidinomethyl)phenoxy]propylamino]-4-benzyloxypyridine-N-oxide (0.94 g) in ethanol (100 ml) was hydrogenated at 344 KPa (50 p.s.i), for 5 hours in the presence of 10% palladium on charcoal (0.1 g). The reaction mixture was filtered and the filtrate evaporated under reduced pressure to give an oil. Trituration under diethyl ether containing a little isopropanol gave as a buff solid 2-[3-[3-(piperidinomethyl)phenoxy]propylamino]-4-hydroxypyridine-N-oxide (0.59 g), m.p. 140°–142.5° C. (recrystallised from isopropanol-acetone).

In another experiment the crude product as an oil was dissolved in chloroform, and treated with phosphorus tribromide to yield the title product (identical by chromatography with the product of Example 1).

EXAMPLE 8

By a method similar to that of Example 1, 3-(3-(piperidinomethyl)phenoxy)propylamine is reacted with:
(a) 5-methyl-2-bromopyrid-4-one,
(b) 6-methyl-2-bromopyrid-4-one, or
(c) 5-benzyl-2-bromopyrid-4-one,
to yield respectively:
(a) 5-methyl-2-[3-[3-(piperidinomethyl)phenoxy]propylamino]pyrid-4-one,
(b) 6-methyl-2-[3-[3-(piperidinomethyl)phenoxy]propylamino]pyrid-4-one, or
(c) 5-benzyl-2-[3-[3-(piperidinomethyl)phenoxy]propylamino]pyrid-4-one.

EXAMPLE 9

By a method similar to that of Example 1, 2-bromopyrid-4-one is reacted with:
(a) 4-(3-(piperidinomethyl)phenoxy)butylamine,
(b) 3-(4-(piperidinomethyl)phenoxy)propylamine,
(c) 3-(3-(2-piperidinoethyl)phenoxy)propylamine,
(d) 3-(3-(dimethylaminomethyl)phenoxy)propylamine, or
(e) 2-(4-(piperidinomethylpyrid-2-yl)methylthio)ethylamine
to yield respectively:
(a) 2-[4-(3-(piperidinomethyl)phenoxy)butylamino]pyrid-4-one,
(b) 2-[3-(4-(piperidinomethyl)phenoxy)propylamino]pyrid-4-one,
(c) 2-[3-(3-(2-piperidinoethyl)phenoxy)propylamino]pyrid-4-one,
(d) 2-[3-(4-(dimethylaminomethyl)phenoxy)propylamino]pyrid-4-one, or
(e) 2-[2-(4-(piperidinomethyl)pyrid-2-ylmethylthio)ethylamino]pyrid-4-one.

EXAMPLE 10

A pharmaceutical composition for oral administration is prepared containing:

|   |   | % by weight |
|---|---|---|
| A | 2-[3-[3-(piperidinomethyl)phenoxy]propylamino]-pyrid-4-one | 55 |
|   | Dibasic calcium phosphate dihydrate | 20 |
|   | Approved colouring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

Other compounds of the invention, for example those specifically described in Examples 2 to 5 can be formulated into pharmaceutical compositions by a similar procedure.

The compounds of this invention, where tested, show no overt signs of toxicity at doses which are a pertinent multiple of the therapeutic dose.

What is claimed is:
1. A compound of the formula (I):

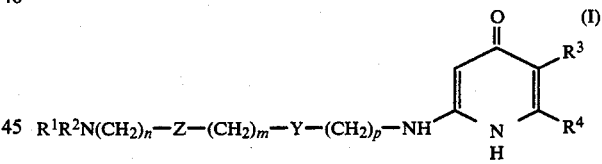

or a pharmaceutically acceptable salt thereof, wherein $R^1$ and $R^2$ together represent —$(CH_2)_q$— wherein q is 4 to 6, to form together with the nitrogen atom to which they are attached a 5–7 membered saturated ring, optionally substituted by $C_{1-6}$alkyl;

n is an integer from 1 to 6;

Z is 1,3-phenylene, 1,4-phenylene, 2,4-pyridyl (wherein the $R^1R^2N(CH_2)_n$ group is in the 4-position);

m is zero or one;

Y is oxygen, sulphur or methylene;

p is two, three or four; and $R^3$ is hydrogen, $C_{1-6}$alkyl or aryl($C_{1-6}$)alkyl and $R^4$ is hydrogen or $C_{1-6}$alkyl.

2. A compound according to claim 1 wherein $R^1R^2N(CH_2)_n$— is piperidinomethyl.

3. A compound according to claim 1 wherein Z is 1,3-phenylene.

4. A compound according to any one of claims 1 to 3 wherein m is zero and Y is oxygen.

5. A compound according to claim 1 which is 3-[3-(3-(piperidinomethyl)phenoxy)propylamino]pyrid-4-one or a pharmaceutically acceptable salt thereof.

6. A compound according to claim 1 which is 2-[3-[3-(pyrrolidinomethyl)phenoxy]propylamino]pyrid-4-one or a pharmaceutically acceptable salt thereof.

7. A compound according to claim 1 which is 2-[3-[3-(hexahydroazepinomethyl)phenoxy]propylamino]pyrid-4-one or a pharmaceutically acceptable salt thereof.

8. A compound according to claim 1 which is 2-[3-[4-(piperidinomethyl)pyrid-2-yloxy]pyropylamino]pyrid-4-one or a pharmaceutically acceptable salt thereof.

9. A compound according to claim 1 which is 2-[3-[3-piperidinomethyl)phenoxy]propylamino]pyrid-4-one dimaleate.

10. A pharamaceutical composition having histamine $H_2$-receptor blocking activity which comprises in an effective amount to block said receptors a compound according to claim 1 and a pharmaceutically acceptable carrier.

11. A pharmaceutical composition having histamine $H_2$-receptor blocking activity which comprises in an effective amount to block said receptors a compound according to claim 5 and a pharmaceutically acceptable carrier.

12. A pharmaceutical composition having histamine $H_2$-receptor blocking activity which comprises in an effective amount to block said receptors a compound according to claim 6 and a pharmaceutically acceptable carrier.

13. A pharmaceutical composition having histamine $H_2$-receptor blocking activity which comprises in an effective amount to block said receptors a compound according to claim 7 and a pharmaceutically acceptable carrier.

14. A pharmaceutical composition having histamine $H_2$-receptor blocking activity which comprises in an effective amount to block said receptors a compound according to claim 8 and a pharmaceutically acceptable carrier.

15. A pharmaceutical composition having histamine $H_2$-receptor blocking activity which comprises in an effective amount to block said receptors a compound according to claim 9 and a pharmaceutically acceptable carrier.

16. A method of blocking histamine $H_2$-receptors which comprises administering to an animal an effective amount to block said receptors of a compound of claim 1.

17. A method of blocking histamine $H_2$-receptors which comprises administering to an animal an effective amount to block said receptors of a compound of claim 5.

18. A method of blocking histamine $H_2$-receptors which comprises administering to an animal an effective amount to block said receptors of a compound of claim 6.

19. A method of blocking histamine $H_2$-receptors which comprises administering to an animal an effective amount to block said receptors of a compound of claim 7.

20. A method of blocking histamine $H_2$-receptors which comprises administering to an animal an effective amount to block said receptors of a compound of claim 8.

21. A method of blocking histamine $H_2$-receptors which comprises administering to an animal an effective amount to block said receptors of a compound of claim 9.

* * * * *